United States Patent
Ishii et al.

(10) Patent No.: US 8,283,489 B2
(45) Date of Patent: Oct. 9, 2012

(54) PROCESS FOR PRODUCING OPTICALLY ACTIVE α-FLUOROCARBOXYLATE

(75) Inventors: Akihiro Ishii, Saitama (JP); Hideyuki Tsuruta, Fujimino (JP); Yuzuru Morino, Ube (JP); Mikihiro Takahashi, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 368 days.

(21) Appl. No.: 12/523,440

(22) PCT Filed: Jan. 8, 2008

(86) PCT No.: PCT/JP2008/050075

§ 371 (c)(1),
(2), (4) Date: Jul. 16, 2009

(87) PCT Pub. No.: WO2008/090755

PCT Pub. Date: Jul. 31, 2008

(65) Prior Publication Data

US 2010/0087673 A1    Apr. 8, 2010

(30) Foreign Application Priority Data

Jan. 23, 2007 (JP) .................. 2007-013020
Aug. 16, 2007 (JP) .................. 2007-212495

(51) Int. Cl.
*C07C 69/63* (2006.01)
(52) U.S. Cl. .................................. 560/227
(58) Field of Classification Search .......... None
See application file for complete search history.

(56) References Cited

U.S. PATENT DOCUMENTS 6,248,889 B1   6/2001   Savu et al.
7,619,111 B2 * 11/2009   Lopez et al. .......... 560/227

2006/0167292 A1   7/2006   Gerlach
2006/0247433 A1   11/2006   Ishii et al.
2008/0071108 A1   3/2008   Lopez et al.

FOREIGN PATENT DOCUMENTS

| EP | 1 780 194 A1 | 5/2007 |
| JP | 2002-530356 A | 9/2002 |
| JP | 2004-323518 A | 11/2004 |
| JP | 2006-83163 A | 3/2006 |
| JP | 2006-083163 A * | 3/2006 |
| JP | 2006-169251 A | 6/2006 |
| JP | 2006-290870 A | 10/2006 |
| WO | WO 2006/018991 A1 | 2/2006 |
| WO | WO 2006/037887 A1 | 4/2006 |

OTHER PUBLICATIONS

International Search Report dated Feb. 5, 2008 with partial translation (Three (3) pages).
PCT/ISA/237 Feb. 5, 2008 (Three (3) pages).
A. Focella et al., "Simple Stereospecific Synthesis of (R)—2-Fluorohexanoic Acid Ethyl Ester", Synthetic Communications, 1991, pp. 2165-2170, vol. 21, No. 21.
Japanese Office Action dated Jun. 26, 2012 (Two (2) pages).
European Search Report dated Dec. 27, 2011 (five (5) pages).
Chinese Office Action dated Feb. 2, 2012 with English Translation (thirteen (13) pages).

* cited by examiner

*Primary Examiner* — Paul A Zucker
(74) *Attorney, Agent, or Firm* — Crowell & Moring LLP

(57) ABSTRACT

An optically active α-fluorocarboxylate is produced by reacting an optically active α-hydroxycarboxylate with sulfuryl fluoride ($SO_2F_2$), trifluoromethanesulfonyl fluoride ($CF_3SO_2F$) or nonafluorobutanesulfonyl fluoride ($C_4F_9SO_2F$) in the presence of organic base and in the absence of reaction solvent. More preferably, a distillation purification is conducted after adding acid to the reaction-terminated liquid. With this, it is possible to produce an optically active α-fluorocarboxylate of a still higher purity. It is possible by this process to advantageously produce an optically active α-fluorocarboxylate on a large-amount scale.

9 Claims, No Drawings

PROCESS FOR PRODUCING OPTICALLY ACTIVE α-FLUOROCARBOXYLATE

TECHNICAL FIELD

The present invention relates to a process for producing an optically active α-fluorocarboxylate, which is an important intermediate of medicines, agricultural chemicals and optical materials.

BACKGROUND OF THE INVENTION

An optically active α-fluorocarboxylate, which is the target of the present invention, is an important intermediate of medicines, agricultural chemicals and optical materials. As publicly known techniques related to the present invention, particularly as practical production processes, it is possible to cite the undermentioned representative four examples. These production processes are in common in that the starting raw material is an optically active α-hydroxycarboxylate having an inverse stereochemistry to the target optically active α-fluorocarboxylate and that a hydroxyl group is converted to a leaving group (stereoretention), and a bimolecular nucleophilic substitution (stereoinversion) is conducted with a fluorine anion.

1) A process (Patent Publication 1) in which an optically active α-hydroxycarboxylate is converted to a chlorosulfite by thionyl chloride, then it is converted to a fluorosulfite by hydrogen fluoride, and finally it is pyrolyzed using a tertiary amine as catalyst.

2) A process (Patent Publication 2) in which an optically active α-hydroxycarboxylate is converted to methanesulfonate by methanesulfonyl chloride in the presence of an organic base, and it is reacted with an alkali metal fluoride.

3) A process (Patent Publication 3) in which an optically active α-hydroxycarboxylate is converted to a trifluoromethanesulfonate by trifluoromethanesulfonyl fluoride in the presence of an organic base, and it is continuously reacted with a salt or complex of the organic base and hydrogen fluoride, which has been produced as a by-product in the reaction system.

4) A process (Patent Publication 4) in which an optically active α-hydroxycarboxylate is converted to a fluorosulfate by sulfuryl fluoride in the presence of an organic base, and it is continuously reacted with a salt or complex of the organic base and hydrogen fluoride, which has been produced as a by-product in the reaction system.
Patent Publication 1: International Application Publication 2006/037887 Pamphlet
Patent Publication 2: Japanese Patent Application Publication 2006-169251
Patent Publication 3: Japanese Patent Application Publication 2006-83163
Patent Publication 4: Japanese Patent Application Publication 2006-290870

SUMMARY OF THE INVENTION

It is an object of the present invention to provide an industrial production process of an optically active α-fluorocarboxylate, which is an important intermediate of medicines, agricultural chemicals and optical materials.

In the processes of Patent Publication 1 and Patent Publication 2, it was necessary to separately conduct at least two reaction steps. Judging from Examples of these, they were processes in which the reaction operations were cumbersome and furthermore waste was in large amount. Therefore, as a result, it was hard to refer them as competitive industrial production processes.

In the processes of Patent Publication 3 and Patent Publication 4, they had a merit that it was possible to continuously conduct in a single reaction container the step of converting it to a trifluoromethanesulfonate or fluorosulfate and the step of replacing it with a fluorine anion (they can be considered to be substantially a single reaction step). However, since the reactions are conducted by using a reaction solvent, and since operations such as extraction and washing are conducted in the post-treatment, although they were industrial production processes, they were production processes that were limited in productivity and that the amount of waste was also larger, as compared with the production process disclosed in the present invention, and had to be reduced.

Thus, there has been a strong demand for a process that is capable of industrially producing an optically active α-fluorocarboxylate.

As a result of an eager study for solving the above-mentioned task, the present inventors have found out that, in a process of reacting an optically active α-hydroxycarboxylate with sulfuryl fluoride, trifluoromethanesulfonyl fluoride or nonafluorobutanesulfonyl fluoride, it is possible to produce an optically active α-fluorocarboxylate with good yield and high optical purity by conducting the reaction in the presence of organic base and in the absence of reaction solvent. Furthermore, the present inventors have clarified that it is possible to easily isolate the optically active α-fluorocarboxylate with high purity by adding acid to the thus obtained reaction-terminated liquid containing the optically active α-fluorocarboxylate and then conducting a distillation purification.

In the present invention, even if the above dehydroxyfluorination reaction is conducted in the absence of reaction solvent, not only there were obtained the results that were satisfactory in yield and operability, but also there were obtained the results that were not inferior, as compared with the case of using reaction solvent, in terms of optical purity, too. Furthermore, impurities that were difficult of separation were not produced as by-products either, even if the reaction is conducted in the absence of reaction solvent.

As a result, it has become possible to greatly reduce an operation for removing the reaction solvent and other coexisting substances after the reaction and to very easily isolate the target substance by directly subjecting the reaction-terminated liquid to a distillation purification.

Furthermore, the present inventors have found out that it is very effective in producing the target substance of high purity to add acid to the reaction-terminated liquid, prior to the distillation purification, and then conduct the distillation. In the present invention, it is inevitable that a small amount of fluoride ions remains in the reaction-terminated liquid. It has been found that separation between this fluoride ion and the target substance is relatively difficult, and its removal from the target substance is difficult, even if a normal distillation treatment is conducted. The present inventors, however, prior to this distillation treatment, added acid to the reaction-terminated liquid and then conducted the distillation. With this, it has become clear that fluoride ions are greatly reduced, and an excessive organic base remaining in the system can also significantly be reduced, and the target substance of a still higher purity can be produced.

Thus, the following two are mentioned as characteristics of the present invention.
1) The target reaction proceeds well under neat condition that reaction solvent is never used, and an optically active α-fluorocarboxylate is obtained with an extremely high optical purity (99% ee or greater in a preferable case) and good yield (Example 1, Example 2, and Example 3).

2) Furthermore, the reaction-terminated liquid is directly subjected to a distillation purification. With this, it is possible to extremely easily recover the optically active α-fluorocarboxylate. Furthermore, upon this, acid is added and then a distillation purification is conducted. With this, it is possible to effectively reduce the organic base content and the fluoride ion concentration in the optically active α-fluorocarboxylate to be recovered (a comparison between Example 2, and Example 1 and Example 3).

According to the present invention, there is provided a process (first process) for producing an optically active α-fluorocarboxylate represented by formula [2]

[Chemical Formula 2]

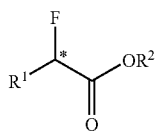

[2]

wherein $R^1$ represents a $C_{1-6}$ alkyl group, $R^2$ represents a $C_{1-4}$ alkyl group, and * represents an asymmetric carbon, the process including reacting an optically active α-hydroxycarboxylate represented by formula [1]

[Chemical Formula 1]

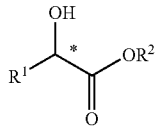

[1]

wherein $R^1$, $R^2$, and * are defined as above, with sulfuryl fluoride ($SO_2F_2$), trifluoromethanesulfonyl fluoride ($CF_3SO_2F$) or nonafluorobutanesulfonyl fluoride ($C_4F_9SO_2F$), in the presence of organic base and in the absence of reaction solvent, wherein stereochemistry of the asymmetric carbon in formula [1] is inverted by the reaction.

The first process may be a process (second process) for producing an optically active 2-fluoropropionate represented by formula [4]

[Chemical Formula 4]

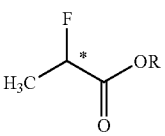

[4]

wherein R represents a methyl group or ethyl group, and * represents an asymmetric carbon, the process including reacting an optically active lactate represented by formula [3]

[Chemical Formula 3]

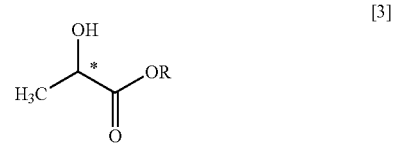

[3]

wherein R and * are defined as above, with sulfuryl fluoride ($SO_2F_2$) or trifluoromethanesulfonyl fluoride ($CF_3SO_2F$), in the presence of an organic base selected from the group consisting of triethylamine, diisopropylethylamine, tri-n-propylamine, tri-n-butylamine, tri-n-pentylamine, tri-n-hexylamine, pyridine, 2,3-lutidine, 2,4-lutidine, 2,6-lutidine, 3,4-lutidine, 3,5-lutidine, 2,4,6-collidine, and 3,5,6-collidine, and in the absence of reaction solvent, wherein stereochemistry of the asymmetric carbon in formula [3] is inverted by the reaction.

The first or second process may be a process (third process) for producing methyl (R)-2-fluoropropionate represented by formula [6]

[Chemical Formula 6]

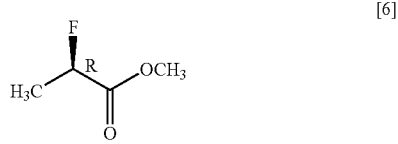

[6]

the process including reacting methyl (S)-lactate represented by formula [5]

[Chemical Formula 5]

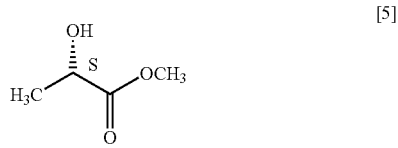

[5]

with sulfuryl fluoride ($SO_2F_2$), in the presence of triethylamine or tri-n-butylamine and in the absence of reaction solvent.

DETAILED DESCRIPTION

By the process of the present invention, it is possible to produce an optically active α-fluorocarboxylate on a large-amount scale. Advantageous points of the present invention as compared with conventional techniques are put together in the following.

As compared with the processes of Patent Publication 1 and Patent Publication 2, the number of reaction steps is smaller, the reaction operation is also easier, and furthermore there is less waste.

As compared with the processes of Patent Publications 3 and Patent Publication 4, it is not necessary at all to use reaction solvent, and the post-treatment operation is extremely easy in a preferable example.

Therefore, in the process of the present invention, it is possible to produce an optically active α-fluorocarboxylate with high productivity and little waste. Thus, it is very useful as an industrial process.

The process for producing an optically active α-fluorocarboxylate of the present invention is explained in detail.

(1) Reaction Step

Firstly, there is explained a reaction step for producing an optically active α-fluorocarboxylate represented by formula [2] by reacting an optically active α-hydroxycarboxylate represented by formula [1] with sulfuryl fluoride, trifluoromethanesulfonyl fluoride or nonafluorobutanesulfonyl fluoride in the presence of organic base and in the absence of reaction solvent.

Regarding stereochemistry of asymmetric carbon of the starting raw material and the target product of the reaction, a step of converting the hydroxyl group to a leaving group proceeds with stereoretention, and a step of conducting a bimolecular nucleophilic substitution reaction with fluorine anion proceeds with stereoinversion. Therefore, S configuration at α position of an optically active α-fluorocarboxylate represented by formula [2] is obtained from R configuration at α position of an optically active α-hydroxycarboxylate represented by formula [1], and similarly R configuration at α position is obtained from S configuration at α position.

As $R^1$ of an optically active α-hydroxycarboxylate represented by formula [1], it is possible to cite methyl group, ethyl group, propyl group, butyl group, amyl group, and hexyl group, and an alkyl group having a carbon number of 3 or more can take a straight-chain or branch. In a preferable example, it is possible to recover an optically active α-fluorocarboxylate represented by formula [2] by directly distilling the reaction-terminated liquid. Upon this, one having a lower boiling point is more easily recovered. Therefore, of those, methyl group, ethyl group, and propyl group are preferable, and particularly methyl group and ethyl group are more preferable.

As $R^2$ of an optically active α-hydroxycarboxylate represented by formula [1], it is possible to cite methyl group, ethyl group, propyl group and butyl group, and an alkyl group having a carbon number of 3 or more can take a straight-chain or branch. Similar to the above, one having a lower boiling point is more easily recovered. Therefore, of those, methyl group and ethyl group are preferable, and particularly methyl group is more preferable. Furthermore, alkyl groups of $R^1$ and $R^2$ can also form a lactone ring by a covalent bond.

Regarding stereochemistry of asymmetric carbon of an optically active α-hydroxycarboxylate represented by formula [1], it can take R configuration or S configuration. Enantiomeric excess (% ee) is not particularly limited. It suffices to use one having 90% ee or greater. Normally, 95% ee or greater is preferable, and particularly 97% ee or greater is more preferable.

An optically active α-hydroxycarboxylate represented by formula [1] can be produced similarly from various optically active α-amino acids on the market, with reference to Synthetic Communications (US), 1991, Volume 21, No. 21, p. 2165-2170. A commercial product was used as methyl (S)-lactate used in Examples.

As a reagent for converting the hydroxyl group to a leaving group, it is possible to cite sulfuryl fluoride, trifluoromethanesulfonyl fluoride, or nonafluorobutanesulfonyl fluoride. Of these, in view of atom economy of fluorine, industrial availability, the post-treatment operation, and waste treatment, sulfuryl fluoride and trifluoromethanesulfonyl fluoride are preferable, and particularly sulfuryl fluoride is more preferable.

Usage of sulfuryl fluoride, trifluoromethanesulfonyl fluoride, or nonafluorobutanesulfonyl fluoride is not particularly limited. It suffices to use 0.7-7 moles relative to 1 mole of an optically active α-hydroxycarboxylate represented by formula [1]. Normally, 0.8-5 moles is preferable, and particularly 0.9-3 moles is more preferable.

The organic base is not particularly limited. As representative ones, it is possible to cite tertiary amines and pyridines. As such organic bases, it is possible to cite trimethylamine, triethylamine, diisopropylethylamine, tri-n-propylamine, tri-n-butylamine, tri-n-pentylamine, tri-n-hexylamine, pyridine, 2,3-lutidine, 2,4-lutidine, 2,5-lutidine, 2,6-lutidine, 3,4-lutidine, 3,5-lutidine, 2,3,4-collidine, 2,4,5-collidine, 2,5,6-collidine, 2,4,6-collidine, 3,4,5-collidine, 3,5,6-collidine, and the like. Of these, preferable are triethylamine, diisopropylethylamine, tri-n-propylamine, tri-n-butylamine, tri-n-pentylamine, tri-n-hexylamine, pyridine, 2,3-lutidine, 2,4-lutidine, 2,6-lutidine, 3,4-lutidine, 3,5-lutidine, 2,4,6-collidine, and 3,5,6-collidine.

In the present invention, the reaction is conducted in the absence of reaction solvent. Therefore, it is important that a salt or complex of the organic base and hydrogen fluoride or a salt or complex of the organic base and $RfSO_3H$ [in the formula, Rf represents a fluorine atom, trifluoromethyl group, or nonafluorobutyl group] has a suitable flow property to make it possible to stir well. As such organic base, particularly triethylamine and tri-n-butylamine are more preferable [Flow property was better in the case of using triethylamine or tri-n-butylamine as the organic base than in the case of using diisopropylethylamine or tri-n-propylamine, as a result of a study on flow property of the obtained reaction-terminated liquid at room temperature by conducting the reaction similar to Examples using methyl (S)-lactate (1.0 eq), sulfuryl fluoride (1.2 eq) and organic base (1.2 eq). See Table-1].

Furthermore, in the distillation operation, it suffices to use one that is different in boiling point at atmospheric pressure from the target compound, optically active α-fluorocarboxylate, by 30° C. or more. Normally 40° C. or more is preferable, and particularly 50° C. or more is more preferable. Furthermore, it is important to select an organic base of which recovery and reuse can easily be conducted. In view of these viewpoints, tri-n-butylamine is extremely preferable in producing methyl (R)-2-fluoropropionate, which is a preferable target compound of the present invention.

TABLE 1

| Organic Base | Reaction-terminated Liquid |
| --- | --- |
| Triethylamine | Liquid Form |
| Diisopropylethylamine | Sherbet Form (Solid-liquid State) |
| Tri-n-propylamine | Solidified |
| Tri-n-butylamine | Liquid Form |

Usage of the organic base is not particularly limited. Relative to 1 mole of optically active α-hydroxycarboxylate represented by formula [1], it suffices to use 0.7-7 moles. Normally 0.8-5 moles is preferable, and particularly 0.9-3 moles is more preferable.

To conduct the reaction in the absence of reaction solvent, which is an important mode of the present invention, refers to that the reaction is conducted by making reaction solvent (liquid such as organic solvent or water) substantially nonexistent in the system, except the above-mentioned reaction reagents. Specifically, it refers to a condition of less than 0.1

L (liter) relative to 1 mole of optically active α-hydroxycarboxylate represented by formula [1]. Normally less than 0.07 L is preferable, and particularly less than 0.05 L is more preferable. A mode of conducting the reaction by not intentionally adding reaction solvent to the system is a representative of conducting the reaction in the absence of reaction solvent and is extremely preferable. By conducting the reaction in the absence of reaction solvent, it is possible to produce optically active α-fluorocarboxylate represented by formula [2] with high productivity and little waste.

Regarding the reaction temperature, since the reaction is conducted in the absence of reaction solvent in the present invention, it is important that a salt or complex of the organic base and hydrogen fluoride or a salt or complex of the organic base and $RfSO_3H$ [in the formula, Rf represents a fluorine atom, trifluoromethyl group or nonafluorobutyl group], which is produced as a by-product in the reaction system, has a suitable flow property and can be stirred well. As such reaction temperature, normally −20 to +70° C. is preferable, and particularly −10 to +50° C. is more preferable. In the case of conducting the reaction at a reaction temperature that is boiling point or higher of sulfuryl fluoride, trifluoromethanesulfonyl fluoride or nonafluorobutanesulfonyl fluoride, it is possible to use a pressure-proof reaction container.

The reaction pressure is not particularly limited. It suffices to conduct that in a range of atmospheric pressure (0.1 MPa) to 2 MPa. Normally atmospheric pressure to 1.5 MPa is preferable, and particularly atmospheric pressure to 1 MPa is more preferable. Therefore, it is preferable to conduct the reaction by using a pressure-proof reaction container made of a material such as stainless steel (SUS) or glass (glass lining).

The reaction time is not particularly limited. It suffices to conduct that in a range of 24 hours or less. It depends on the starting material, the organic base, the reactant for converting the hydroxyl group to a leaving group, the reaction conditions, etc. Therefore, it is preferable to monitor the condition of the reaction progress by an analytical means such as gas chromatography, thin-layer chromatography, liquid chromatography, or nuclear magnetic resonance (NMR) and judge the time when the starting raw material has almost disappeared as being end point.

(2) Distillation Step

An optically active α-fluorocarboxylate obtained by the above-mentioned reaction step can be isolated by subsequently subjecting it to purification step (post-treatment). This purification means is not particularly limited. In the present invention, however, reaction solvent is not used. Therefore, it is possible to distill the reaction-terminated liquid directly (as it is without conducting a particular purification operation). That is particularly preferable. As mentioned above, in the reaction of the present invention, impurities that are difficult of separation are almost not produced even under a condition in the absence of reaction solvent. Therefore, even if the reaction-terminated liquid is directly subjected to distillation step, it is possible to recover the target optically active α-fluorocarboxylate represented by formula [2] with high purity and high optical purity. In the following, this distillation step is explained.

As the conditions of the distillation, in view of the boiling point, a person skilled in the art can suitably set pressure and bath temperature (tank temperature). Distillation under reduced pressure is preferable since it is possible to moderately reduce the distillation temperature. In the case of conducting distillation under reduced pressure, the degree of pressure reduction (It refers to absolute pressure in the system upon distillation. It is the same hereinafter) is not particularly limited. It suffices to conduct that in a range of less than atmospheric pressure. Normally 50 kPa or less is preferable, and particularly 25 kPa or less is more preferable. If it is lower than 0.1 kPa, separation efficiency of the distillation lowers, and it becomes rather disadvantageous in operation in some cases. Therefore, it is not preferable. Therefore, it is a preferable mode to conduct the distillation in a range of, for example, 0.5 kPa to 25 kPa.

Furthermore, the column top temperature in the distillation depends on the above-mentioned degree of pressure reduction. Of course, the bath temperature is set at a temperature that is higher than this column top temperature. The bath temperature also gets to depend on the degree of pressure reduction. This temperature is in a range of 200° C. or lower. Normally 175° C. or lower is preferable, and particularly 150° C. or lower is more preferable. The bath temperature does not have the lower limit. However, when the distillation is conducted at a bath temperature of 20° C. or higher, more preferably 40° C. or higher, the distillation tends to become stable. It is therefore advantageous. Accordingly, a bath temperature of 20-175° C. is taken as a preferable temperature, and 40-150° C. is a still more preferable temperature.

According to need, the recovered distillate is subjected to a fractional distillation. With this, it is possible to obtain the target product with higher purity.

In the present invention, it is possible to recover and reuse the organic base used in the reaction. If the reaction and the distillation are conducted under preferable operation conditions, it is possible to recover from the tank residue (distillation residue) the organic base after use in the form of a salt or complex with $RfSO_3H$ [in the formula, Rf represents a fluorine atom, trifluoromethyl group or nonafluorobutyl group] (a mixture with $RfSO_3H$) or a salt or complex with hydrogen fluoride (a mixture with hydrogen fluoride) (mostly in the form of the former). The tank residue is neutralized with an alkaline aqueous solution prepared from sodium hydroxide, potassium hydroxide, calcium hydroxide, or the like. The liberated organic base is separated. According to need, washing with water or dehydration operation is conducted, followed by distillation. With this, it is possible to recover the organic base with high chemical purity and good yield. The recovered organic base can be reused without lowering of the reactivity. In the case of conducting the recovery and the reuse by such method, an organic base that is high in fat-solubility and easy in dehydration is preferable. Naturally, the method of the recovery and the reuse is not limited to the above-mentioned technique.

The above distillation step can still more preferably be conducted by conducting it after adding acid to the reaction-terminated liquid. That is, acid is added to the reaction-terminated liquid, and the resulting liquid is subjected to the distillation step. With this, it was found that the organic base used in the reaction and the remaining fluoride ions are effectively removed, and optically active α-fluorocarboxylate represented by formula [2] can be produced with higher purity, high productivity and less waste.

As such acid, it is possible to use inorganic acid or organic acid. In particular, an acid that does not exist as aqueous solution and is low in volatility is still more preferable. As such inorganic acid, it is possible to cite sulfuric acid, phosphoric acid, boric acid, etc. As the organic acid, it is possible to cite formic acid, methanesulfonic acid, trifluoromethanesulfonic acid, acetic acid, trifluoroacetic acid, trichloroacetic acid, oxalic acid, propionic acid, acrylic acid, malonic acid, butyric acid, methacrylic acid, succinic acid, maleic acid, fumaric acid, malic acid, tartaric acid, valeric acid, hexanoic acid, benzoic acid, o-, m- or p-fluorobenzoic acid, o-, m- or p-chlorobenzoic acid, o-, m- or p-hydroxybenzoic acid, p-toluenesulfonic acid, o-, m- or p-toluic acid, o-, m- or p-anisic acid, o-, m- or p-benzenedicarboxylic acid (phthalic acid, isophthalic acid or terephthalic acid), etc. Of these, organic acid is preferable due to its high capability for removing fluoride ions. Particularly, benzoic acid is more preferable.

Usage of the acid is not particularly limited. It suffices to use 0.7-9 moles relative to 1 mole of the organic base used excessively. Normally, 0.8-7 moles is preferable, and particularly 0.9-5 moles is more preferable (for example, in Example 2, the organic base used excessively is in 0.27 mol, and the acid has been used in 0.62 mol, meaning that it has been used in 2.30 eq).

In the present invention, it is a particularly preferable mode to add the organic acid to the reaction-terminated liquid and then conduct a distillation purification under reduced pressure, in producing the optically active 2-fluoropropionate.

Furthermore, in the present invention, particularly preferable modes are a method in which optically active lactate represented by formula [3] is reacted with sulfuryl fluoride ($SO_2F_2$) or trifluoromethanesulfonyl fluoride ($CF_3SO_2F$), in the presence of an organic base selected from triethylamine, diisopropylethylamine, tri-n-propylamine, tri-n-butylamine, tri-n-pentylamine, tri-n-hexylamine, pyridine, 2,3-lutidine, 2,4-lutidine, 2,6-lutidine, 3,4-lutidine, 3,5-lutidine, 2,4,6-collidine, and 3,5,6-collidine, and in the absence of reaction solvent, thereby obtaining optically active 2-fluoropropionate represented by formula [4], and a method in which an organic acid is added to the reaction-terminated liquid containing optically active 2-fluoropropionate represented by formula [4] and obtained by the above method, followed by conducting a distillation purification under reduced pressure, since usefulness of the product is conspicuous and since advantageous effect of the present invention is conspicuous.

Furthermore, extremely preferable modes are a method in which methyl (S)-lactate represented by formula [5] is reacted with sulfuryl fluoride ($SO_2F_2$) in the presence of an organic base selected from triethylamine and tri-n-butylamine and in the absence of reaction solvent to obtain methyl (R)-2-fluoropropionate represented by formula [6], and a method in which benzoic acid is added to the reaction-terminated liquid containing methyl (R)-2-fluoropropionate represented by formula [6] and obtained by the above method, followed by conducting a distillation purification under reduced pressure, due to that usefulness of the product is conspicuous, that getting hold of the raw material compound is particularly easy, that advantageous effect of the present invention is conspicuous, etc.

Embodiments of the present invention are specifically explained by the following examples, but the present invention is not limited to these examples.

Example 1

A stainless steel (SUS), pressure-proof, reaction container was charged with 12.0 g (115 mmol, 1.00 eq, optical purity 99.0% ee or higher) of methyl (S)-lactate represented by the following formula

[Chemical Formula 7]

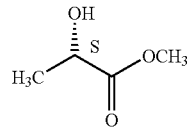

and 13.0 g (128 mmol, 1.11 eq) of triethylamine, followed by cooling in a refrigerant bath of −20° C. and then bubbling from a cylinder 13.5 g (132 mmol, 1.15 eq) of sulfuryl fluoride ($SO_2F_2$). The inside temperature was gradually increased to room temperature, followed by stirring at the same temperature for 2 hours and 30 minutes. Conversion of the reaction was found to be 95% or higher by determination by gas chromatography.

Then, the reaction-terminated liquid was directly subjected to a distillation under reduced pressure (degree of pressure reduction; 15 kPa, bath temperature; 70° C.), thereby obtaining 10.3 g of a distillate of methyl (R)-2-fluoropropionate represented by the following formula.

[Chemical Formula 8]

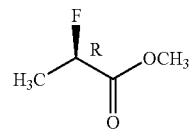

Recovery percentage was 84%. Chemical purity (calculated by gas chromatography), optical purity [calculated by gas chromatography; the ester group is subjected to hydride reduction to convert that to (R)-2-fluoropropanol, and its Mosher ester is analyzed], triethylamine content (calculated by $^1$H-NMR), and fluoride ion concentration of the distillate were respectively 94.2%, 99.0% ee or higher, 3.8 mol %, and 342 ppm.

$^1$H and $^{19}$F-NMR spectrums of methyl (R)-2-fluoropropionate are shown in the following.

$^1$H-NMR [standard substance; $(CH_3)_4Si$, deuterated solvent; $CDCl_3$], δ ppm; 1.59 (dd, 23.6 Hz, 6.8 Hz, 3H), 3.81 (s, 3H), 5.03 (dq, 48.6 Hz, 6.9 Hz, 1H).

$^{19}$F-NMR (standard substance; $C_6F_6$, deuterated solvent; $CDCl_3$), δ ppm; −22.77 (dq, 47.2 Hz, 23.8 Hz, 1F).

Example 2

A stainless steel (SUS), pressure-proof, reaction container was charged with 258 g (2.48 mol, 1.00 eq, optical purity 99.0% ee or higher) of methyl (S)-lactate represented by the following formula

[Chemical Formula 9]

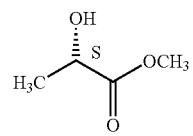

and 278 g (2.75 mol, 1.11 eq) of triethylamine, followed by bubbling from a cylinder 280 g (2.74 mol, 1.10 eq) of sulfuryl fluoride ($SO_2F_2$) while controlling the inside temperature in 0-11° C. The inside temperature was gradually increased to room temperature, followed by stirring at the same temperature for all night. Conversion of the reaction was found to be 92% by determination by gas chromatography.

Then, 76 g (0.62 mol, 2.30 eq relative to triethylamine used excessively) of benzoic acid was added to the reaction-terminated liquid, and it was subjected to a distillation under reduce pressure (degree of pressure reduction; 1.5 kPa, bath temperature; 70° C.), thereby obtaining 193 g of a distillate of methyl (R)-2-fluoropropionate represented by the following formula.

[Chemical Formula 10]

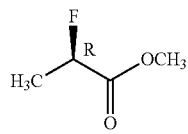

Recovery percentage was 73%. Chemical purity (calculated by gas chromatography), optical purity [calculated by gas chromatography; the ester group is subjected to hydride reduction to convert that to (R)-2-fluoropropanol, and its Mosher ester is analyzed], triethylamine content (calculated by $^1$H-NMR), and fluoride ion concentration of the distillate were respectively 97.3%, 99.5% ee, a trace amount (less than 0.2 mol %), and 89 ppm.

$^1$H and $^{19}$F-NMR spectrums of methyl (R)-2-fluoropropionate were the same as those of Example 1.

In such a manner, it was possible in Example 2 to further greatly reduce triethylamine content and fluoride ion content by conducting the distillation after adding acid to the reaction-terminated liquid, as compared with Example 1.

Example 3

A stainless steel (SUS), pressure-proof, reaction container was charged with 106.8 kg (1.026 kmol, 1.00 eq, optical purity 99.0% ee) of methyl (S)-lactate represented by the following formula

[Chemical Formula 11]

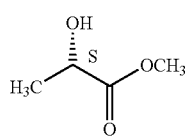

and 190.1 kg (1.026 kmol, 1.00 eq) of tri-n-butylamine, followed by cooling with a circulation-type refrigerant of −10° C. and bubbling from a cylinder 105.1 kg (1.030 kmol, 1.00 eq) of sulfuryl fluoride ($SO_2F_2$). The inside temperature was gradually increased to room temperature, and stirring was conducted at the same temperature for 4 hours. Conversion of the reaction was found to be 95% by determination by $^1$H-NMR.

Then, the reaction-terminated liquid was directly subjected to a distillation under reduced pressure (degree of pressure reduction; 1.0 kPa, bath temperature; 75° C.).

With this, 95.4 kg of a distillate of methyl (R)-2-fluoropropionate represented by the following formula

[Chemical Formula 12]

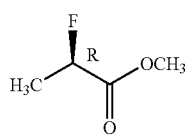

was obtained. Recovery percentage was 84%. Chemical purity (calculated by gas chromatography), optical purity [calculated by chiral gas chromatography], tri-n-butylamine content (calculated by gas chromatography), fluoride ion concentration and water content of the distillate were respectively 96.5%, 97.4% ee, 1.5%, 543 ppm, and 317 ppm.

$^1$H and $^{19}$F-NMR spectrums of methyl (R)-2-fluoropropionate were the same as those of Example 1.

560 kg of water was added to the tank residue (distillation residue), followed by cooling with a circulation-type refrigerant of 0° C. 48% sodium hydroxide aqueous solution was added until pH became 12. The liberated organic layer was subjected to a two-layer separation. The recovered organic layer was washed with 105 kg of water. Then, a fractional distillation (column top temperature 79-82° C., degree of pressure reduction 14-16 hPa) was conducted by using a distillation apparatus made of glass (the number of theoretical plates: 15), thereby recovering 156 kg of a main distillate (chemical purity: 99.9% or higher, water content: less than 0.1%) (recovery percentage: 82%). It was possible to reuse the recovered tri-n-butylamine without lowering of reactivity.

The invention claimed is:

1. A process for producing an optically active α-fluorocarboxylate represented by formula [2]

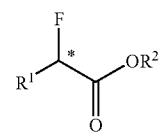

[2]

wherein $R^1$ represents a $C_{1-6}$ alkyl group, $R^2$ represents a $C_{1-4}$ alkyl group, and * represents an asymmetric carbon, the process comprising reacting an optically active α-hydroxycarboxylate represented by formula [1]

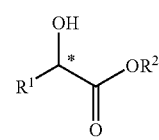

[1]

wherein $R^1$, $R^2$ and * are defined as above, with sulfuryl fluoride ($SO_2F_2$), trifluoromethanesulfonyl fluoride ($CF_3SO_2F$) or nonafluorobutanesulfonyl fluoride ($C_4F_9SO_2F$), in the presence of organic base and in the absence of reaction solvent, wherein stereochemistry of the asymmetric carbon in formula [1] is inverted by the reaction.

2. A process according to claim 1, wherein a distillation purification is conducted after adding an acid to a reaction-terminated liquid that has been obtained by the reaction according to claim 1 and that contains the optically active α-fluorocarboxylate.

3. A process according to claim 2, wherein the acid is an organic acid.

4. A process for producing an optically active 2-fluoropropionate represented by formula [4]

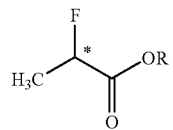

[4]

wherein R represents a methyl group or ethyl group, and * represents an asymmetric carbon, the process comprising reacting an optically active lactate represented by formula [3]

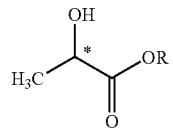

[3]

wherein R and * are defined as above, with sulfuryl fluoride (SO$_2$F$_2$) or trifluoromethanesulfonyl fluoride (CF$_3$SO$_2$F), in the presence of an organic base selected from the group consisting of triethylamine, diisopropylethylamine, tri-n-propylamine, tri-n-butylamine, tri-n-pentylamine, tri-n-hexylamine, pyridine, 2,3-lutidine, 2,4-lutidine, 2,6-lutidine, 3,4-lutidine, 3,5-lutidine, 2,4,6-collidine, and 3,5,6-collidine, and in the absence of reaction solvent wherein stereochemistry of the asymmetric carbon in formula [3] is inverted by the reaction.

5. A process according to claim 4, wherein a distillation purification under reduced pressure is conducted after adding an organic acid to a reaction-terminated liquid that has been obtained by the reaction according to claim 4 and that contains the optically active 2-fluoropropionate.

6. A process for producing methyl (R)-2-fluoropropionate represented by formula [6]

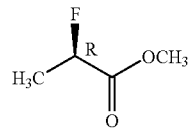

[6]

the process comprising reacting methyl (S)-lactate represented by formula [5]

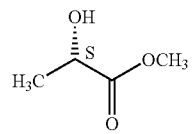

[5]

with sulfuryl fluoride (SO$_2$F$_2$), in the presence of triethylamine or tri-n-butylamine and in the absence of reaction solvent.

7. A process according to claim 6, wherein a distillation purification under reduced pressure is conducted after adding benzoic acid to a reaction-terminated liquid that has been obtained by the reaction according to claim 6 and that contains the methyl (R)-2-fluoropropionate.

8. A process according to claim 1, wherein a distillation purification under reduced pressure is conducted after adding benzoic acid to a reaction-terminated liquid that has been obtained by the reaction according to claim 1 and that contains the optically active α-fluorocarboxylate.

9. A process according to claim 4, wherein a distillation purification under reduced pressure is conducted after adding benzoic acid to a reaction-terminated liquid that has been obtained by the reaction according to claim 4 and that contains the optically active 2-fluoropropionate.

* * * * *